United States Patent [19]

Osbon

[11] Patent Number: 4,856,498
[45] Date of Patent: Aug. 15, 1989

[54] VACUUM GENERATING AND CONSTRICTION APPARATUS FOR AUGMENTING MALE POTENCY

[75] Inventor: Julian W. Osbon, Augusta, Ga.

[73] Assignee: Osbon Medical Systems, Ltd., Augusta, Ga.

[21] Appl. No.: 31,706

[22] Filed: Mar. 30, 1987

[51] Int. Cl.$^4$ ................................................. A61F 5/41
[52] U.S. Cl. ................................... 128/79; 128/303 A
[58] Field of Search .............. 128/79, 303 A; 285/235

[56] References Cited

U.S. PATENT DOCUMENTS

| 1,225,341 | 5/1917 | Lederer | 128/79 |
| 3,421,504 | 1/1969 | Gibbons | 128/79 |
| 4,378,008 | 3/1983 | Osbon, Sr. | 128/79 |
| 4,539,980 | 4/1985 | Chaney | 128/303 A |

FOREIGN PATENT DOCUMENTS

| 148586 | 7/1985 | European Pat. Off. | 128/79 |
| 98794 | 10/1961 | Norway | 285/235 |
| 2129688 | 5/1984 | United Kingdom | 128/79 |

*Primary Examiner*—Gene Mancene
*Assistant Examiner*—Cary E. Stone
*Attorney, Agent, or Firm*—Shanley and Baker

[57] ABSTRACT

Improved vacuum generating and constriction apparatus with user adaptablity including provision of an adapter insert for changing the effective internal diameter of the entry end of a vacuum chamber, an improved constriction means having a generally circular periphery with elongated handle unitary at a single end with an inner toroidal ring, improved vacuum seal connector and a hand pump which fixedly locates an on/off valve for controlling the vacuum.

5 Claims, 2 Drawing Sheets

VACUUM GENERATING AND CONSTRICTION APPARATUS FOR AUGMENTING MALE POTENCY

This invention relates to new and improved apparatus for augmenting male sexual potency by helping to induce and maintain penile erection for sexual intercourse. In its more specific aspects, the invention is concerned with vacuum generating and constriction apparatus adaptable to different user requirements having features which make the apparatus easier to use and more effective during use.

Vacuum generating devices for augmenting male potency which evacuate a cylinder placed over the male organ, and thereby induce blood engorgement, are known; the use of constriction bands to retain the engorgement is also known; see, for example, U.S. Pat. No. 4,378,008 Erection Aid Device issued on Mar. 29, 1983. When properly used, such devices have certain advantages over penile surgical implants, or sheaths or other forms of exterior organ extenders or supports worn during sexual relations since, respectively, they do not require invasive surgery and do not require artificial barriers between the parties during use.

However, one shortcoming, which made the vacuum type of apparatus less than fully satisfactory prior to the present invention, is that the vacuum cylinder could not be adjusted to different users' requirements. Also, with the prior arrangement of parts the apparatus could be somewhat awkward to use in the establishment or releasing of the vacuum; also, comfortable and easy to handle constriction means for maintaining the vacuum induced engorgement were not previously available.

Facilitating use by different individuals, having differing individual physical and subjective requirements, results in adaptability and effectiveness which are highly important contributions of the invention. Additionally, since through continued use of the apparatus a previously inactive individual's needs change, adaptability to differing physical requirements becomes more important. The use of a dimensionally adaptable vacuum generating and constriction apparatus has also been found to be advantageous because of the need for each user to experiment in arriving at his own subjectively satisfactory arrangement and because of a user's concerns about privacy. Also, the invention contributes simplicity and economy while providing dimensionally adaptable features.

Other advantages and contributions of the invention are considered in more detail in relation to the following drawings, wherein.

Figure 1:
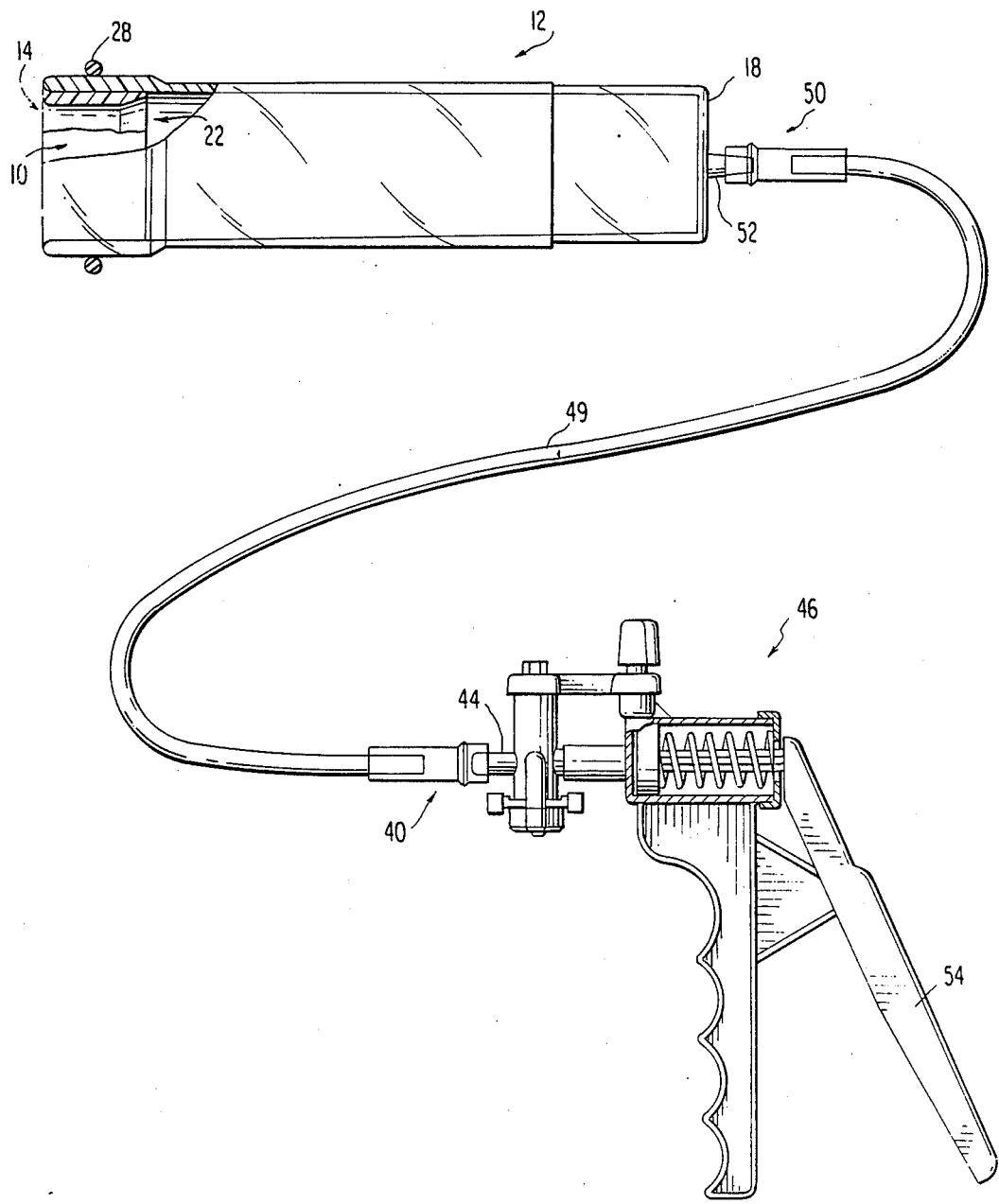
FIG. 1 is a general arrangement view, with portions in longitudinal cross section of an improved apparatus for augmenting male potency in accordance with the invention.

The improved vacuum generating and constriction apparatus of FIG. 1 combines an elongated, cylindrical-configuration vacuum chamber with an adapter at its entrance end, connectors for flexible tubing, a vacuum hand pump and stretchable constriction band means.

One unique dimensionally-adaptable feature comprises a tubular-configuration adapter 10 which has an external diameter enabling it to fit snugly, as shown in FIG. 1, into vacuum chamber 12 at the organ receiving end 14 of such cylindrically shaped chamber. Providing a plurality of adapters of the type shown enables dimensional adjustment of the effective internal opening at the organ receiving end of such vacuum cylinder. Making differing internal diameters available enables more efficient operation by providing a closer fit for more effective vacuum attainment and retention, and quicker air evacuation of the vacuum chamber; while also accommodating differing user requirements.

The elongated vacuum chamber of generally cylindrical configuration (cylinder) 12 is made of rigid material such as transparent plexiglas acrylic plastic. Such vacuum cylinder is open at its end which is proximal to the user for receiving the organ. It is substantially closed at its distal end save for a small-diameter tubular fitting suitable for connection with flexible tubing. As discussed in more detail later, special receptacle-connector means are used in combination with the flexible tubing to establish pneumatic communication between the vacuum chamber and a hand pump vacuum source.

Additionally, providing for selection and use of adapter inserts of differing internal diameters avoids problems of an overly large diameter vacuum cylinder which can result in scrotal tissue being drawn up into the vacuum cylinder, causing user discomfort.

The exterior diameter and length of tubular adapters as taught by the invention are selected to enable an adapter to be positioned quickly and easily, and nest securely, within the open end 14 of vacuum cylinder 12 before the vacuum cylinder is placed over the organ. The adapter 10 has a flange 16 (FIG. 2) at its end confronting the user so as to provide an extended surface area for contacting the abdominal skin at the base of the organ; this helps to provide an improved vacuum seal between the receiving end of the vacuum means and the user.

The vacuum chamber 12 has a smooth interior surface along its length which can be tapered slightly along such length in approaching the closed distal end 18. Vacuum chamber 12 has a thicker gauge portion 20 at its open end, after which its exterior diameter is tapered slightly toward closed distal end 18. Such slight tapering facilitates molding of such vacuum chambers which have a generally cylindrical appearance so that the term vacuum cylinder as used herein is reasonably descriptive and apt.

The sidewall of the vacuum cylinder 12 is approximately $\frac{1}{8}$ inch thick in approaching distal end 18. The outside diameter in a typical embodiment of the vacuum cylinder can be from approximately two (2) inches at such distal end (18) and approximately two and a quarter (2.25) inches at collar 20 which is proximal to the user; length provided is sufficient to provide adequate space for generating a vacuum during engorgement.

Figure 2:
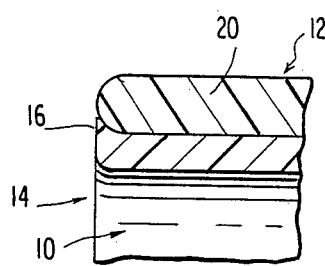
FIGS. 2 and 3 are enlarged cross sectional views of portions of the apparatus of FIG. 1.

The tubular adapter insert 10 is also made from a suitable rigid material, preferably a transparent plastic such as plexiglass acrylic. It is adapted to fit easily and securely within the vacuum cylinder 12 at open end 14. The flange 16, at the end of the adapter 10, which contacts the user extends radially outwardly with a radius which is partially dependent on the internal diameter of the insert; typically flange 16 (FIG. 2) would have a radial measurement of approximately $\frac{3}{8}$ to $\frac{5}{8}$ inch. Flange 16 is adapted to be flush with and to contact the edge of the vacuum cylinder 12 at its open end 14, as shown in FIG. 2.

The tubular adapter 10 is approximately one and one half (1.5) inches long. The effective diameter contiguous to the open end 14 of cylinder 12 is decreased dependent on the internal diameter of the adapter selected.

Figure 3:
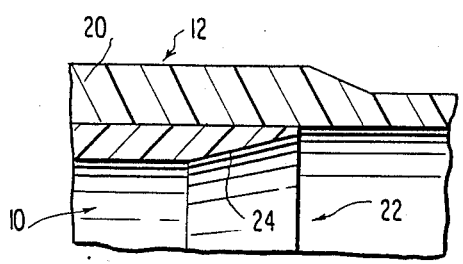

Adapter 10 has a configuration at its distal end 22, as shown in FIG. 3, which presents a smooth gradually tapered surface 24 allowing comfortable relative movement of the organ at the interface of the adapter 10 and the interior surface of vacuum cylinder 12. Surface 24 also provides a fingertip contact for easy removal of the adapter insert from its nested position, such as for cleaning, or for the use of the vacuum cylinder alone, or with a different insert.

A constriction band 28 is shown in FIG. 1. A plurality of such bands made of elastic material having stretchable rubber characteristics, such as natural latex rubber for softness and resilience, are made available. The invention teaches a special configuration shown in plan view in FIG. 4. When unstretched such bands are generally of circular peripheral configuration in plan view and have a generally rounded configuration in radial cross section (FIG. 1). Several constriction bands of different stretch characteristics and dimensions are provided for use with the apparatus to accommodate different user requirements. The user can employ one, or more of the different stretch characteristic bands in varying combinations, to arrive at the appropriate constriction for effective retention of engorgement while providing for comfort and avoidance of skin irritation. Bands of different inside diameter (when unstretched) help to provide differences in the constrictive force applied and are useful in adaptation to different user requirements.

Figure 4:
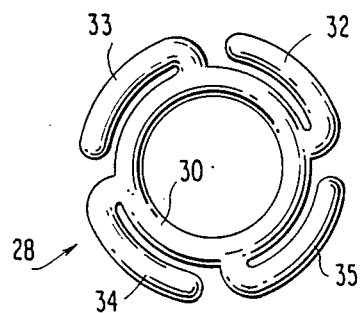
FIG. 4 is a plan view of a new stretchable constriction means forming part of the invention.

Elongated, handle means are provided about the outer periphery of toroidal configuration ring 30 (FIG. 4). With use of handle portions which are unitary at a single longitudinal end with the internal ring 30, band 28 can be conveniently moved from the end of the vacuum cylinder onto the organ of the user; and band 28 can be comfortably moved along such organ. This configuration, in a unique way, enables the elongated handle portions 32, 33, 34 and 35 to fit within the organ receiving end of the vacuum means (insert or cylinder).

Bands of differing inner toroid diameters (starting at about ¾ inch) and differing stretch properties are provided. Constriction bands with differing characteristics can be differently colored or otherwise marked for user convenience. It has been found that combinations of different bands can be used to enable selection of a gradient of constriction characteristics for rapidly accommodating different user requirements. The constriction devices are sufficiently elastic to be stretched around the proximal end of the vacuum cylinder. After engorgement of the organ, the constriction means (one or more bands 18) are slid from the vacuum cylinder and onto the base of the organ in order to retain the blood engorgement of the organ.

The elongated curved portion of a handle leading to its free end is closely spaced to and concentric with the center ring 30 thus providing adaptability not previously available in attempts to make constriction bands more convenient to use. The elongated concentric handle portions are unitary at a single end which along with the configuration enables such handles to fit more readily within the organ-receiving end of the vacuum means. Therefore the generally circular configuration for the constriction bands, as shown in FIG. 4, has an added advantage facilitating adaptable use should it be desired to partially increase vacuum or engorgement after the constriction band is in place on the organ. That is, additional vacuum can be applied when a constriction band is in place around the base of an organ because the outer circumference of a band, with the configurations taught, can be readily fitted within the receiving end of the insert or cylinder, so as to permit added or more effective vacuum. The improved contact with the surrounding abdominal skin surface resulting from such interfitting of the constriction means can improve the vacuum seal.

Figure 5:
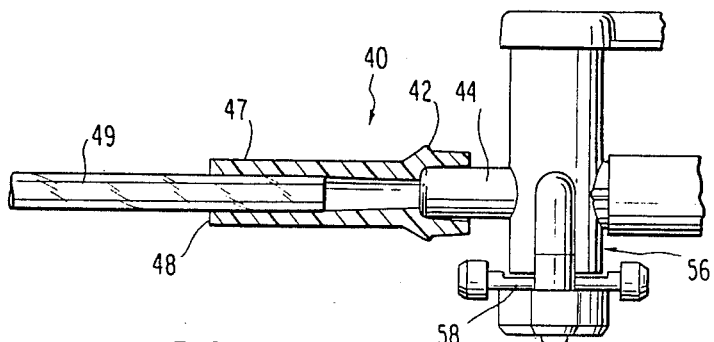
FIG. 5 is an enlarged cross-section view of a portion of the vacuum pump and connector apparatus of FIG. 1.

Special plastic connectors are provided for use between longitudinal ends of the flexible tubing and, respectively, the vacuum cylinder distal end fitting and the vacuum pump tubular fitting. The elongated connectors act as receptacles at each of their ends permitting a tight fit and a seal which improves under vacuum. Such receptacle connectors have a truncated conical internal shapes at each end as illustrated by FIG. 5; i.e., the inner diameter decreases in progressing longitudinally from each longitudinal end toward the longitudinally central portion; this provides a truncated conical configuration of each end of a connector. The receptacle connectors can be made of a flexible transparent plastic, such as polyvinyl chloride; the flexible tubing can be made of a plastic such as vinyl. One connector can be glued to the flexible tubing at each longitudinal end of the flexible tubing; but is not necessary for vacuum seal purposes with the internal configuration taught.

Referring to FIG. 5, connector 40 includes a flanged end 42 for connection to a rigid fitting such as vacuum tubular fitting 44 on vacuum pump 46. An elongated tubular portion 47 of connector 40 extends from such flanged end of the connector toward distal end 48. Flexible hollow tubing 49 fits within such elongated portion 47. The internal diameter at the flanged end 42 decreases in the direction the vacuum fitting 44 is inserted; and at the opposite end of connector 40, the internal diameter at elongated tubular portion 47 decreases in the direction flexible tube 49 is inserted. The receptacle-connector 50, used with the small-diameter fitting on vacuum cylinder 12 has the same configuration as described above and is connected between the flexible hollow tubing 18 and the small-diameter fitting 52 at the substantially closed end 18 of vacuum chamber 12.

Use of hand pump 46 efficiently produces an effective vacuum; the pistol grip action made available enables easy reciprocation of a piston in an evacuation cylinder by movement of handle 54. On/off valve means are integral with the hand pump avoiding the awkwardness of working with a valve positioned along the hollow flexible tubing, as was the previous practice. A vacuum control valve 56, shown schematically in FIG. 5, is actuated by movement of control arm 58 along a cam surface. Release of vacuum in cylinder 12 cam thus be readily provided at the appropriate time for removal of the cylinder.

While specific materials, dimensions and apparatus have been set forth for purposes of description, it is to be understood that substitutions or modifications are available in the light of the above teachings; therefore, the scope of the present invention is to be determined with reference to the appended claims.

I claim:

1. An improved vacuum generating and constriction apparatus for augmenting male potency, comprising in combination:

an elongated, generally cylindrical configuration vacuum chamber of sufficient size to cover a male sex organ, such chamber being open at one longitudinal end thereof for receiving such organ and having pneumatic connector means contiguous to its opposite longitudinal end;

a tubular-configuration organ adapter means suitable for nestably fitting within the open end of such vacuum chamber so as to be retained within such cylindrical vacuum chamber contiguous to its open end and to effectively reduce the size of such open end for accommodating different user needs, such adapter means having a proximal end for contact with a user, such adapter means presenting at its proximal end a flange extending radially outwardly of its internal surface tubular configuration at such open end of the cylindrical-configuration vacuum chamber to provide an extended surface area for contact with such user;

vacuum source means for evacuating such cylindrical-configuration chamber;

means for establishing pneumatic communication between such pneumatic connector means of the cylindrical-configuration vacuum chamber and such vacuum source means;

vacuum control means located on such vacuum source means for controlling generation, maintenance and release of a vacuum in such cylindrical-configuration vacuum chamber, and stretchable elastic means of generally toroidal configuration having an inner diameter adapted to constrictive contact around the base of the male organ so as to retain blood engorgement in such organ contemporaneously with releasing vacuum in such cylindrical vacuum chamber.

2. The apparatus of claim 1 in which such adapter means, at its remaining distal end opposite to its proximal end, presents a smooth inside tubular surface tapering radially outwardly toward the inside tubular surface of such cylindrical configuration vacuum chamber.

3. The apparatus of claim 1 in which such elastic means comprises a circular configuration stretchable inner ring, and unitary stretchable handle means, such handle means including a plurality of elongated individual handles which are unitary with such ring at a single end thereof and include radially exterior handle portions substantially concentrically oriented in relation to such ring;

such ring and handle means being coplanar so as to be substantially planar when not in use with such handle portions defining a generally circular peripheral configuration.

4. The apparatus of claim 3 in which such generally circular peripheral configuration of such handle portions enable such elastic constriction means to fit within such open end defined by such cylindrical configuration vacuum chamber or within the proximal end of such adapter means.

5. A unitary stretchable constriction means formed from elastic material such as natural or synthetic rubber, such constriction means having a generally circular peripheral configuration in plan view with portions thereof coplanar when not in use, comprising a toroidal configuration inner ring of predetermined interior diameter adapted for constrictive contact around the base of a male organ so as to retain blood engorgement in such organ after releasing vacuum in an associated vacuum generating and organ constriction apparatus, and at least a pair of elongated handles presenting a generally circular configuration over a major portion of their lengths, such circular configuration portion of such handles being substantially concentric with such inner ring when not in use; and with a single longitudinal end of each such elongated handle means being unitary with such inner ring.

* * * * *